(12) United States Patent
Daumas et al.

(10) Patent No.: US 7,358,371 B2
(45) Date of Patent: Apr. 15, 2008

(54) PROCESS FOR THE PREPARATION OF 1,5—CARBOXYLIC ACID DERIVATIVES

(75) Inventors: Marc Daumas, Oraison (FR); Philippe Vayron, Chateauneuf de Chabre (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/548,008

(22) Filed: Oct. 10, 2006

(65) Prior Publication Data

US 2007/0099978 A1 May 3, 2007

Related U.S. Application Data

(63) Continuation of application No. PCT/FR05/01155, filed on May 10, 2005.

(30) Foreign Application Priority Data

May 10, 2004 (FR) .................................. 04 05057

(51) Int. Cl.
C07D 231/10 (2006.01)
(52) U.S. Cl. .................. 548/374.1; 548/375.1
(58) Field of Classification Search ............. 548/374.1, 548/375.1
See application file for complete search history.

(56) References Cited

U.S. PATENT DOCUMENTS 5,079,370 A * 1/1992 D'Silva et al. .......... 548/366.7

FOREIGN PATENT DOCUMENTS

| EP | 0576357 | 3/1997 |
|---|---|---|
| WO | WO 01/40195 | 6/2001 |

OTHER PUBLICATIONS

Cottineau, B., et al., Database Beilstein Beilstein Institute for Organic Chemistry reaction ID 9056190; 9007797; 9007899; 9007844, Syn. Lett. vol. 5, (2002) pp. 769-770.
D'Alessio, R., et al., Synthesis and Immunosuppressive Activity of Novel Prodigiosin Derivatives , J. Med. Chem. vol. 43, (2000) pp. 2257-2565.
Noro, M., et. al., Silver Halide Photographic Material Containing Polymethyne Pyrazolone Dye, Chemical Abstracts Service, Database Accession No. 1998:198072 compounds with m: 205499-56-5,205499-57-6, 205499-58-7 & JP10083041.
Raimundo, B.C., et. al., Integrating Fragment Assembly and Biophysical Methods in the Chemical Advancement of Small-Molecule Antagonists of IL-2: An Approaching for Inhibiting Protein-Protein Interactions, J. Med. chem. (2004) vol. 47, pp. 3111-3130.
Regan, J., et. al., Pyrazole Urea-Based Inhibitors of P38 MAP Kinase; From Lead Compound to Clinical Candidate, J. Med. Chem. vol. 45, (2002) pp. 2994-3008.
Wang, X.-J., et. al., Cross-Coupling of 1-Aryl-5-Bromopyrazoles: Regioselective Synthesis of 3,5-Disubstituted 1-Arylpyrazoles, Tetrahedron Letters vol. 41, (2000) pp. 4713-4716.

* cited by examiner

Primary Examiner—Kamal A. Saeed
(74) Attorney, Agent, or Firm—Balaram Gupta

(57) ABSTRACT

The present invention comprises a process for the preparation of compounds that possess an affinity for the cannabinoid receptor in the human brain. These compounds are useful as immunomodulators and psychotropic agents in the treatment of thymic disorders, vomiting, myo-relaxation, various types of neuropathy, memory disorders, dyskinesia, migraine, asthma, epilepsy, glaucoma, anticancer chemotherapy, in ischemia and angina, in orthostatic hypotension and in cardiac distress. More specifically, the present invention comprises a process for the preparation of a series of compounds of formula (I):

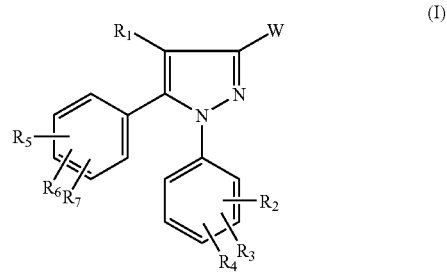

in which $R_1$-$R_7$ and W represent various alkyl groups and the derivatives thereof and are more specifically are defined herein.

17 Claims, No Drawings

PROCESS FOR THE PREPARATION OF 1,5—CARBOXYLIC ACID DERIVATIVES

CROSS-REFERENCE TO RELATED APPLICATIONS

This application is a continuation of International Application No.
PCT/FR2005/001155 filed on May 10, 2005 which is incorporated herein by reference in its' entirety which also claims the benefit of priority of French Patent Application No. 04/05,057 filed on May 10, 2004.

FIELD OF THE INVENTION

The present invention relates generally to processes for the preparation of pharmaceutical compounds and compositions useful in the treatment of disorders and diseases of the central nervous system (CNS). More specifically, the present invention relates to the preparation of compounds that have a strong affinity for the cannabinoid receptor and which are therefore particularly valuable in the therapeutic areas in which cannabis is known to be involved such as disorders of the immune system, the central nervous system and the cardiovascular or endocrine systems. More specifically, the present invention relates to a novel process for preparing 1,5-diphenylpyrazole-3-carboxylic acid derivatives.

BACKGROUND OF THE INVENTION 1,5-Diphenyl-4-methylpyrazole-3-carboxylic acid esters are described in particular in European Patent EP 576 357 and U.S. Pat. No. 5,624,941 to Barth et. al., both of which are hereby incorporated by reference. These esters are useful intermediates for preparing 1,5-diphenyl-4-methylpyrazole-3-carboxylic acid derivatives that are cannabinoid $CB_1$ receptor antagonists.

It has now been found that the pyrazoles formed by the process of the present invention have an excellent affinity for the cannabinoid receptor and are therefore particularly valuable in the therapeutic areas for diseases and disorders in which cannabis is known to be involved.

The effects of cannabinoids are due to an interaction with specific high-affinity receptors present in the central nervous system (Devane et al., Molecular Pharmacology, 1988, 34, 605-613) and peripheral nervous system (Nye et al., The Journal of Pharmacology and Experimental Therapeutics, 1985, 234, 784-791; Kaminski et al., 1992, Molecular Pharmacology, 42, 736-742; Munro et al., Nature, 1993, 365, 61-65).

Characterization of this receptor has been made possible by the development of specific synthetic ligands such as the agonists WIN 55212-2 (J. Pharmacol. Exp. Ther., 1993, 264, 1352-1363) or CP 55,940 (J. Pharmacol. Exp. Ther., 1988, 247, 1046-1051).

The therapeutic indications of cannabinoids pertain to a variety of areas such as the immune system, the central nervous system and the cardiovascular or endocrine system (Hollister, Pharmacological Reviews, 1986, 38, 1-20, Renv and Sinha, Progress in Drug Research, 1991, 36, 71-114, Cannabinoid receptor expression in human leucocytes, European Journal of Biochemistry, 1993, 214, 173-180.

More particularly, compounds possessing an affinity for the cannabinoid receptor are useful as immunomodulators and psychotropic agents in treatment of thymic disorders, vomiting, myo-relaxation, various types of neuropathy, memory disorders, dyskinesia, migraine, asthma, epilepsy and glaucoma, in anticancer chemotherapy, in ischemia and angina, in orthostatic hypotension and in cardiac distress.

More particularly, ethyl 5-(4-chlorophenyl)-1-(2,4-dichlorophenyl)-4-methylpyazol-3-carboxylate, described in European Patent EP 656 354, is a useful intermediate for preparing N-piperidino-5-4-chlorophenyl)-1-(2,4-dichlorophenyl)-4-methylpyrazole-3-carboxamide, generically known as ribonabant.

SUMMARY OF THE INVENTION

The present invention comprises a process for the preparation of compounds that possess an affinity for the cannabinoid receptor in the human brain. These compounds are useful as immunomodulators and psychotropic agents in the treatment of thymic disorders, vomiting, myo-relaxation, various types of neuropathy, memory disorders, dyskinesia, migraine, asthma, epilepsy and glaucoma, anticancer chemotherapy, in ischemia and angina, in orthostatic hypotension and in cardiac distress. More specifically, the present invention comprises a process for the preparation of a series of compounds of formula (I):

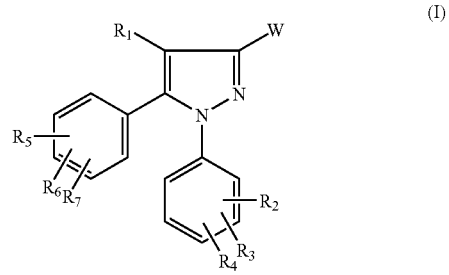

in which $R_1$-$R_7$ and W are defined herein.

DETAILED DESCRIPTION OF THE INVENTION

The subject of the present invention is a process for preparing a series of compounds of formula (I):

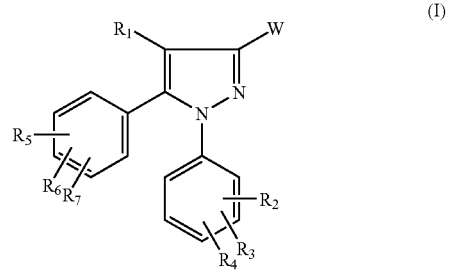

in which:
W represents a group —COOR or a radical —CN;
$R_1$ represents a hydrogen or halogen atom or a $(C_1$-$C_4)$ alkyl group;
$R_2$, $R_3$, $R_4$, $R_5$, $R_6$ and $R_7$ each represent, independently of one another a hydrogen or halogen atom or a $(C_1$-$C_4)$alkyl, $(C_1$-$C_4)$alkoxy or trifluoromethyl group;
R represents a $(C_1$-$C_4)$alkyl or benzyl group;

characterized in that a phenylboronic acid derivative of formula (II):

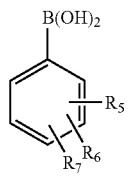
(II)

in which $R_5$, $R_6$ and $R_7$ are as defined for (I), is reacted, in a solvent, in the presence of a catalyst in a basic medium, with a compound of formula (III):

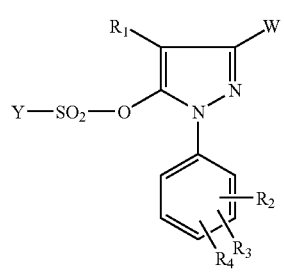
(III)

in which:

W, $R_1$, $R_2$, $R_3$ and $R_4$ are as defined for structure (I);

Y represents a $(C_1-C_4)$alkyl group, a $(C_1-C_4)$perfluoroalkyl group or a phenyl group that is unsubstituted or substituted with a methyl, chloro or nitro group.

Particularly, a subject of the present invention is a process for preparing a compound of formula (IA):

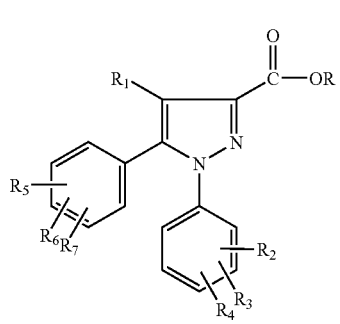
(IA)

in which:

$R_1$, $R_2$, $R_3$, $R_4$, $R_5$, $R_6$, $R_7$ and R are as defined for a compound of formula (I);

characterized in that a phenylboronic acid derivative of formula (II) as defined above is reacted, in a solvent, in the presence of a catalyst in a basic medium, with a compound of formula (IIIA):

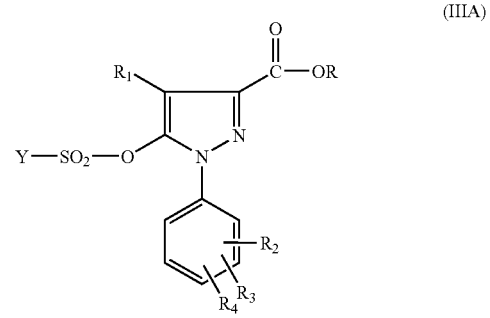
(IIIA)

in which:

Y, R, $R_1$, $R_2$, $R_3$ and $R_4$ are as defined above.

More specifically, the present claimed invention is in particular also a process for preparing a compound of formula (IB):

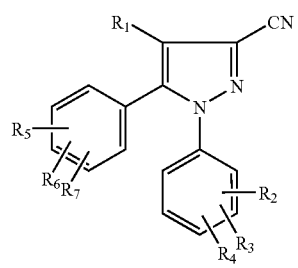
(IB)

in which:

$R_1$, $R_2$, $R_3$, $R_4$, $R_5$, $R_6$ and $R_7$ are as defined for a compound of formula (I);

characterized in that a phenylboronic acid derivative of formula (II) as defined above is reacted, in a solvent, in the presence of a catalyst in a basic medium, with a compound of formula (IIIB):

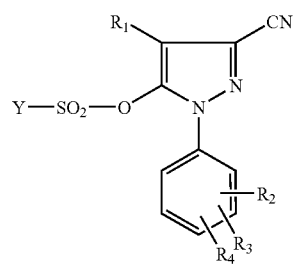
(IIIB)

in which:

Y, $R_1$, $R_2$, $R_3$ and $R_4$ are as defined above.

Preferably, the reaction of a compound of formula (II) with a compound of formula (III), (IIIA) or (IIIB) is carried out in an aromatic solvent, for example toluene, or in an ethereal solvent, for example tetrahydrofuran or dimethoxyethane or in dioxane, in the presence of a palladium complex such as tetra-cis(triphenylphosphine)palladium, and in a basic medium, for example in the presence of an alkali metal carbonate, such as sodium carbonate or potassium carbonate.

According to a preferred embodiment, the reaction is carried out in a two-phase medium, in the presence of tetra-cis(triphenylphosphine)palladium, the basic medium consisting of sodium carbonate in an aqueous solution.

According to a preferred process for preparing a compound of formula (I), a phenylboronic acid derivative of formula (II) is reacted with a compound of formula (III) in which Y represents a group $CF_3$, namely a compound of formula:

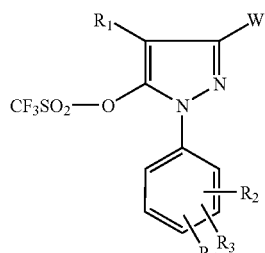

(III: Y = $CF_3$)

In addition, according to a preferred process for preparing a compound of formula (IA), a phenylboronic acid derivative of formula (II) is reacted with a compound of formula (IIIA) in which Y represents a group $CF_3$, namely a compound of formula:

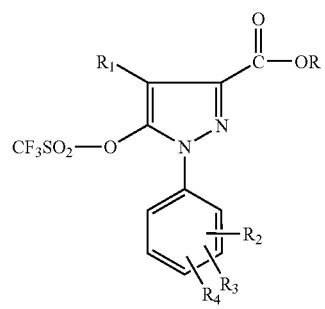

(IIIA: Y = $CF_3$)

Finally, according to a preferred process for preparing a compound of formula (IB), a phenylboronic acid derivative of formula (II) is reacted with a compound of formula (IIIB) in which Y represents a group $CF_3$, namely a compound of formula:

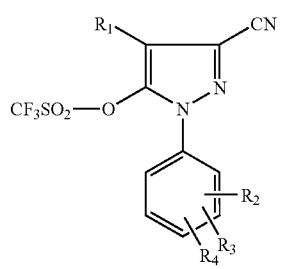

(IIIB: Y = $CF_3$)

More preferably, 4-chlorophenylboronic acid is reacted with a compound of formula (IIIAa):

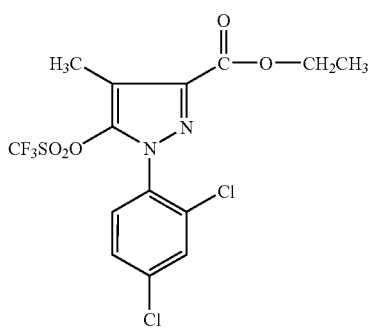

Also more preferably, 4-bromophenylboronic acid is reacted with a compound of formula (IIIAb):

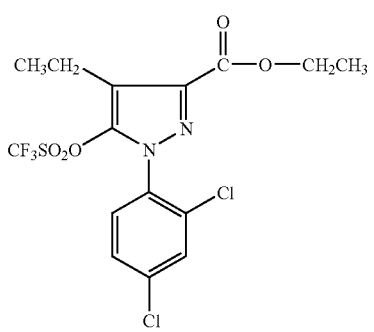

Even more preferably, 4-chlorophenylboronic acid is reacted with a compound of formula (IIIBa):

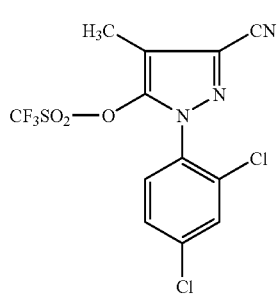

Finally, more preferably, 4-bromophenylboronic acid is reacted with a compound of formula (IIIBb):

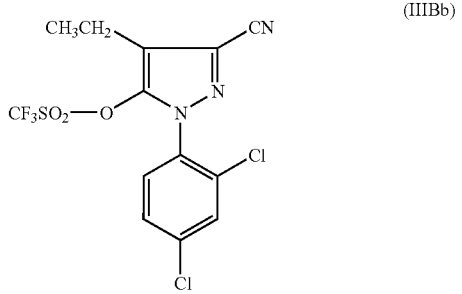

(IIIBb)

The compound of formula (III) is synthesized from a pyrazolone derivative of formula (IV):

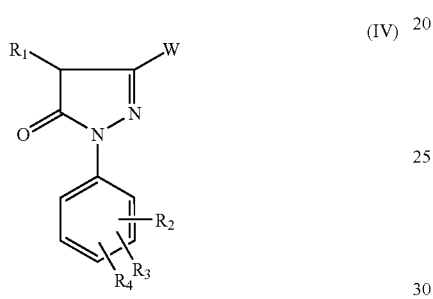

(IV)

In particular, the compound of formula (IIIA) is derived from a pyrazolone derivative of formula (IVA):

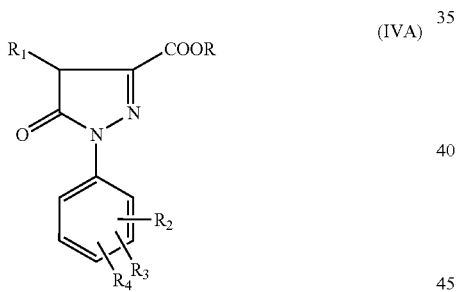

(IVA)

Also in particular, the compound of formula (IIIB) is synthesized from a pyrazolone derivative of formula:

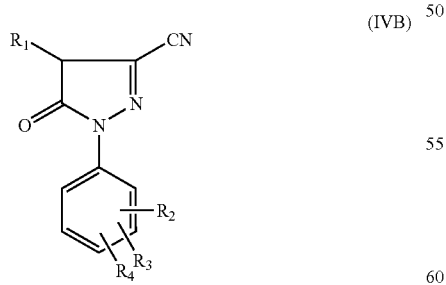

(IVB)

To prepare a compound of formula (III), (IIIA) or (IIIB), an anhydride of formula $(YSO_2)_2O$ or a chloride of formula $YSO_2Cl$ is reacted with a compound of formula (IV), (IVA) or (IVB), the reaction being carried out in the presence of a base, preferably a tertiary amine.

In particular, the compound of formula:

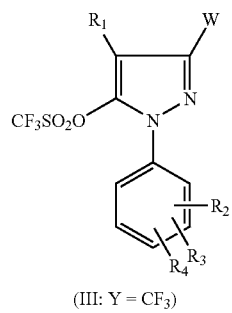

(III: Y = $CF_3$)

is obtained by reaction of triflic anhydride with a pyrazolone derivative of formula:

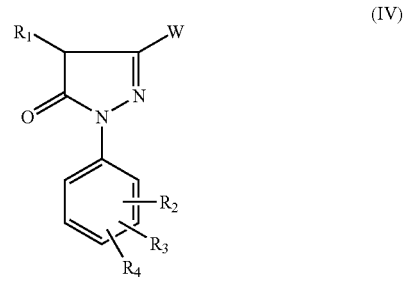

(IV)

in the presence of a base, such as a tertiary amine, and in a solvent, such as dichloromethane.

Also in particular, the compound of formula:

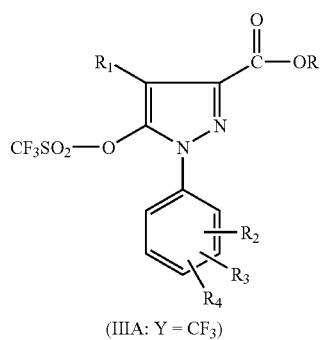

(IIIA: Y = $CF_3$)

may also be prepared through the reaction of triflic anhydride with a pyrazolone derivative of formula (IVA):

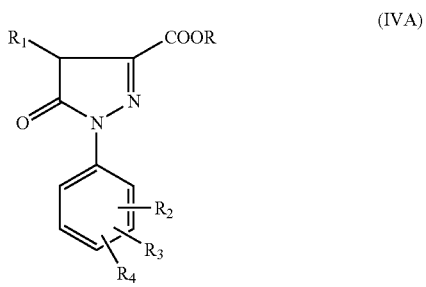

(IVA)

in the presence of a base, such as a tertiary amine, and in a solvent, such as dichloromethane.

Finally in particular, the compound of formula:

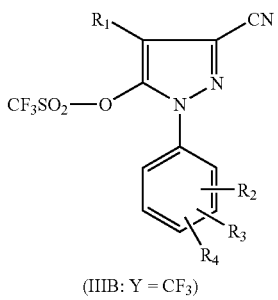

(IIIB: Y = CF₃)

may also be synthesized by the reaction of triflic anhydride with a pyrazole derivative of formula (IVB):

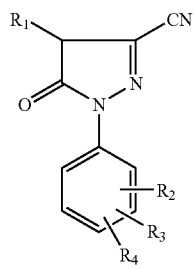

(IVB)

in the presence of a base, such as a tertiary amine, and in a solvent, such as dichloromethane.

Preferably, the compound of formula (III), (IIIA) or (IIIB), in which Y represents $CF_3$, is synthesized by the reaction of triflic anhydride with triethylamine in an equimolecular mixture, in dichloromethane, at a temperature of between $-5°$ C. and $+5°$ C.

The compound of formula (IV):

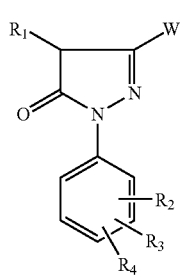

(IV)

may be prepared by the reaction of a hydrazine derivative of formula (V):

(V)

in which $R_2$, $R_3$ and $R_4$ are as defined for (I), with a derivative of formula (VI):

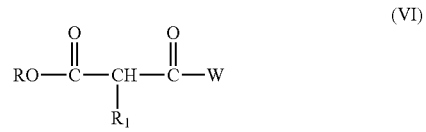

(VI)

in which R, $R_1$ and W are as defined above for (I).

In particular, the compound of formula (IVA):

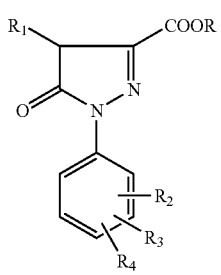

(IVA)

is obtained by reaction of a hydrazine derivative of formula (V) with a derivative of formula (VIA):

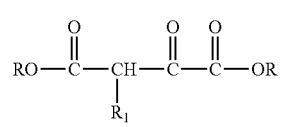

(VIA)

Also in particular, the compound of formula (VIB):

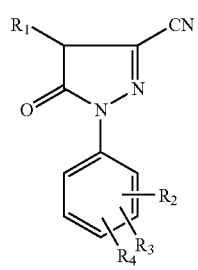

(IVB)

is obtained by the reaction of a hydrazine derivative of formula (V) with a derivative of formula:

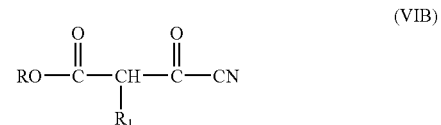

(VIB)

Preferably, a hydrazine hydrochloride of formula (V) is used in a solvent, preferably, an acid medium, for example, acetic acid; or in toluene in the presence of hydrochloric acid, acetic acid or trifluoroacetic acid.

The 3-oxosuccinate derivatives of formula (VI), (VIA) or (VIB) are known or are prepared by known methods such as Claisen condensation of an ester enolate with an oxalic acid ester.

The compound of formula (IV) can exist in 2 tautomeric forms:

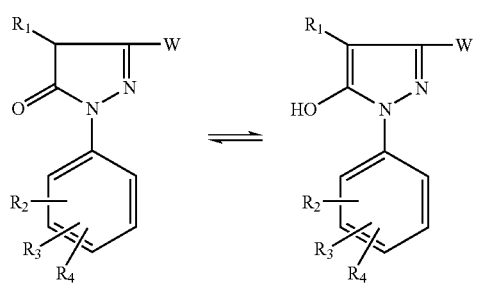

In another embodiment, a subject of the present invention are compounds of formula (III):

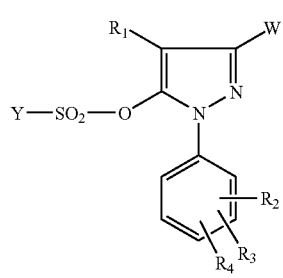

(III)

in which:
- W represents a group —COOR or a radical —CN;
- Y represents a ($C_1$-$C_4$)alkyl group, a ($C_1$-$C_4$)perfluoroalkyl group or a phenyl group that is unsubstituted or substituted with a methyl-, chloro- or nitro- group;
- $R_1$ represents a hydrogen or halogen atom or a ($C_1$-$C_4$) alkyl group;
- $R_2$, $R_3$ and $R_4$ each represent, independently of one another, a hydrogen or halogen atom or a ($C_1$-$C_4$)alkyl, ($C_1$-$C_4$)alkoxy or trifluoromethyl group;
- R represents a ($C_1$-$C_4$)alkyl or benzyl group.

Preferably, another embodiment of the present invention are compounds of formula:

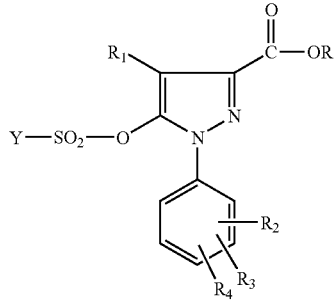

(IIIA)

in which:
Y, R, $R_1$, $R_2$, $R_3$ and $R_4$ are as defined above.

More preferably, yet another embodiment of the present invention are compounds of formula(IIIB):

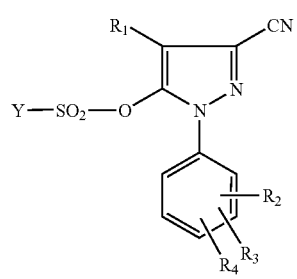

(IIIB)

in which:
Y, $R_1$, $R_2$, $R_3$ and $R_4$ are as defined above.

More preferably, a subject of the present invention is the compound of formula:

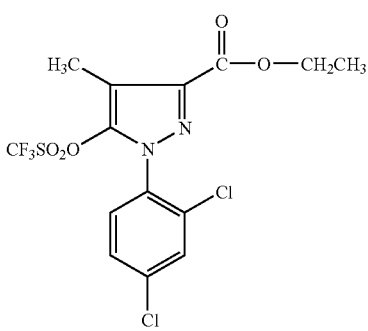

(IIIAa)

Also more preferably, a subject of the present invention is the compound of formula:

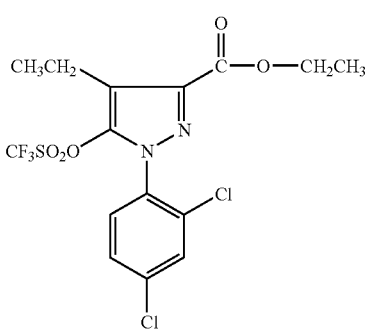

(IIIAb)

Even more preferably, a subject of the present invention is the compound of formula:

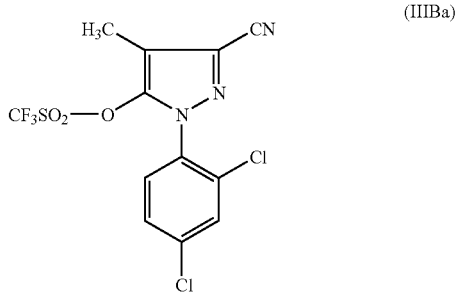
(IIIBa)

Finally more preferably, a subject of the present invention is a compound of formula:

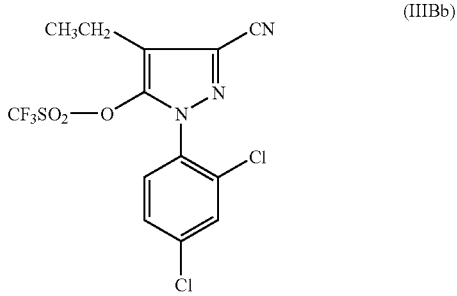
(IIIBb)

The following examples are disclosed in order to teach one skilled in the art how to more specifically and successfully carry out the processes and embodiments of the present invention. They are for illustrative purposes only, and should not be construed as limiting the spirit and scope of the invention as later delineated and defined by the claims that follow.

EXAMPLE 1

The signals observed in NMR are expressed in The mass spectra are measured in the electrospray (ES) ionization mode. The signals observed in NMR are expressed in the following way: s:singlet; bs:broad singlet; d:doublet; sd:split doublet; t:triplet; st:split triplet; q:quartet; m:unresolved peak; mt:multiplet.

A) Preparation of ethyl 5-(4-chlorophenyl)-1-(2,4-dichlorophenyl)-4-methyl-1H-pyrazole-3-carboxylate Ethyl 1-(2,4-dichlorophenyl)-4-methyl-5-oxo-4,5-dihydro-1H-pyrazole-3-carboxylate 2,4-dichlorophenylhydrazine hydrochloride(12.6 g) is dissolved in 100 ml of toluene and this solution is placed under nitrogen; after stirring, 10 g of diethyl 2-methyl-3-oxosuccinate are added and the mixture is then heated and 5 ml of TFA are added at 55° C. The mixture is left at the reflux of the solvent for 4 and a half hours, with stirring. The mixture is allowed to return to ambient temperature and is then heated to 75° C. and the reaction medium is hydrolyzed with 30 ml of water. The mixture is separated by settling out, the aqueous phase is discarded and the organic phase is then evaporated in order to eliminate the residual TFA. The organic phase is taken up with 10 ml of toluene and the expected product then crystallizes, m=10.2 g.

ES⁻: [M—H]⁻=313.0.
NMR (DMSO-d6 1H at 300 MHz): 1.26 ppm: t: 3H; 2.11 ppm: s: 3H; 4.23 ppm: q: 2H; 7.57 ppm: m: 2H; 7.87 ppm: bs: 1H; 11.04 ppm: bs: 1H.

B) Ethyl 1-(2,4-dichlorophenyl)-4-methyl-5-(((trifluoromethyl)sulphonyl)oxy)-1H-pyrazole-3-carboxylate Pyrazolone (5.0 gm) obtained in the preceding step is suspended in 25 ml of DCM, under nitrogen, and the mixture is cooled to 0° C. with stirring. 2.4 ml of TEA followed by 3 ml of triflic anhydride are added and the stirring is maintained at 0° C. for 15 minutes. The reaction medium is hydrolyzed with 20 ml of DCM. The reaction medium is separated by settling out and the organic phase is then washed with 20 ml of water. The aqueous phase is discarded. The organic phase is evaporated and the oil obtained is chromatographed on silica, elution being carried out with a pentane/EtOAc mixture (90/10; v/v). The fractions containing the expected compound are combined and evaporated to dryness. 6.77 g of the expected product are obtained.
ES⁺: [M+Na]⁺=468.8
NMR (DMSO-d6 1H at 300 MHz): 1.31 ppm: t: 3H; 2.27 ppm: s: 3H; 4.34 ppm: q: 2H; 7.72 ppm: sd: 1H; 7.79 ppm: d: 1H; 8.04 ppm: d: 1H.

C) Ethyl 5-(4-chlorophenyl)-1-(2,4-dichlorophenyl)-4-methyl-1H-pyrazole-3-carboxylate 2.55 g of the pyrazole triflate of the preceding step, 1.08 g of 4-chlorophenylboronic acid and 67 mg of tetrakis (triphenylphosphine)palladium are mixed, under nitrogen; 25 ml of toluene and 7.1 ml of a 2M aqueous sodium carbonate solution are added. The reaction medium is stirred at 65° C. for 6 hours.
The reaction medium is separated by settling out, the aqueous phase is discarded, and the organic phase is then washed with 10 ml of water. After separation by settling out, the organic phase is evaporated off. The product obtained is purified by chromatography on silica, elution being carried out with a cyclohexane/EtOAc mixture (85/15; v/v). 1.890 g of the expected compound are obtained.
NMR (DMSO-d6 1H at 300 MHz): 1.31 ppm: t: 3H; 2.23 ppm: s: 3H; 4.32 ppm: q: 2H; 7.24 ppm: d: 2H; 7.46 ppm: d: 2H; 7.57 ppm: sd: 1H; 7.73 ppm: d: 1H; 7.77: d: 1H.

What is claimed is:
1. A process for the preparation of a compound of formula (I):

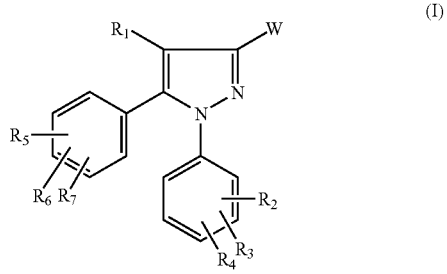
(I)

in which:
W represents a group —COOR or a radical —CN;
R₁ represents a hydrogen or halogen atom or a (C₁-C₄) alkyl group;
R₂, R₃, R₄, R₅, R₆ and R₇ each represent, independently of one another a hydrogen or halogen atom or a (C₁-C₄) alkyl, (C₁-C₄) alkoxy or trifluoromethyl group;
R represents a (C₁-C₄) alkyl or benzyl group;
wherein a phenylboronic acid derivative of formula (II):

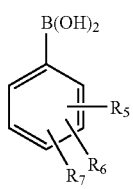

(II)

in which $R_5$, $R_6$ and $R_7$ are as defined above for (I), is reacted with a compound of formula (III):

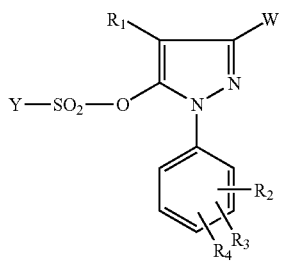

(III)

in which:
W, $R_1$, $R_2$, $R_3$ and $R_4$ are as defined above for (I);
Y represents a $(C_1\text{-}C_4)$alkyl group, a $(C_1\text{-}C_4)$ perfluoroalkyl group or a phenyl group that is un-substituted or substituted with a methyl, chloro or nitro group.

2. The process according to claim 1, for preparing a compound of formula (IA):

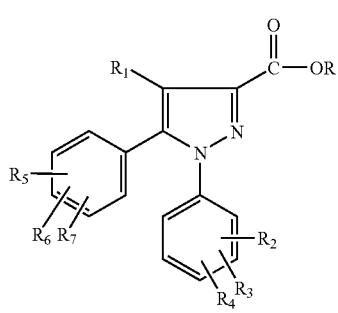

(IA)

in which:
$R_1$, $R_2$, $R_3$, $R_4$, $R_5$, $R_6$, $R_7$ and R are as defined for a compound of formula (I) in claim 1;
wherein a phenylboronic acid derivative of formula (II) as defined in claim 1 is reacted with a compound of formula (IIIA):

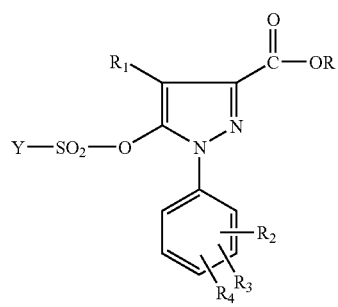

(IIIA)

in which:
Y, R, $R_1$, $R_2$, $R_3$ and $R_4$ are as defined with respect to formula I in claim 1.

3. The process as recited in claim 1 for the preparation of a compound of formula (IB):

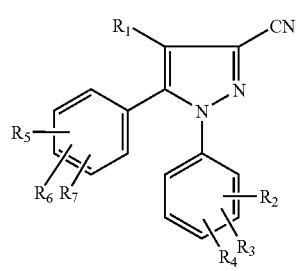

(IB)

in which
$R_1$, $R_2$, $R_3$, $R_4$, $R_5$, $R_6$ and $R_7$ are as defined for a compound of formula (I) in claim 1;
wherein a phenylboronic acid derivative of formula (II) as defined in claim 1 is reacted with a compound of formula (IIIB):

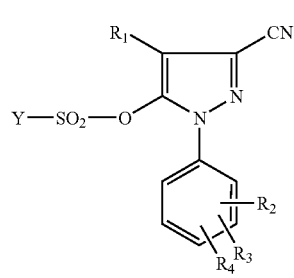

(IIIB)

in which:
Y, $R_1$, $R_2$, $R_3$ and $R_4$ are as defined in claim 1.

4. The process according to claim 1, wherein a phenylboronic acid derivative of formula (II) as defined in claim 1 is reacted with a compound of formula (III):

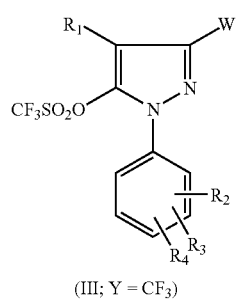

(III; Y = CF$_3$)

in which:
W, $R_1$, $R_2$, $R_3$ and $R_4$ are as defined in claim 1.

5. The process according to claim 2, wherein a phenylboronic acid derivative of formula (II) as defined in claim 1 is reacted with a compound of formula (IIIA);

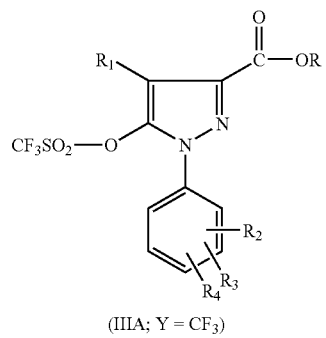

(IIIA; Y = CF₃)

in which:

R, $R_1$, $R_2$, $R_3$ and $R_4$ are as defined in claim 1.

6. The process as recited in claim 3, wherein a phenylboronic acid derivative of formula (II) as defined in claim 1 is reacted with a compound of formula (IIIB):

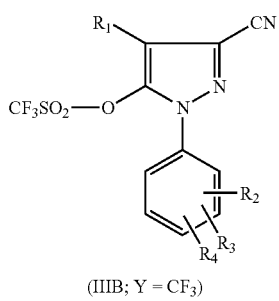

(IIIB; Y = CF₃)

in which:

$R_1$, $R_2$, $R_3$ and $R_4$ are as defined in claim 1.

7. The process according to claim 5, wherein 4-chlorophenylboronic acid is reacted with a compound of formula (IIIAa):

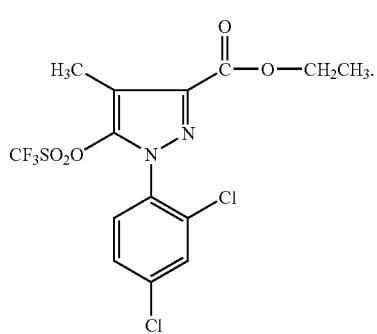

(IIIAa)

8. The process as recited in claim 5, wherein 4-bromophenylboronic acid is reacted with a compound of formula (IIIAb):

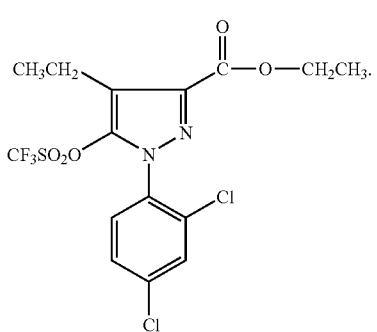

(IIIAb)

9. The process according to claim 6, wherein 4-chlorophenylboronic acid is reacted with a compound of formula (IIIBa):

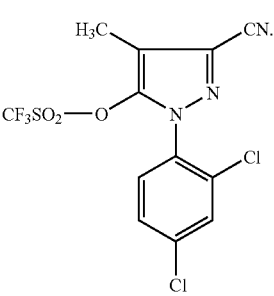

(IIIBa)

10. The process as recited in claim 6, wherein 4-bromophenylboronic acid is reacted with a compound of formula (IIIBb):

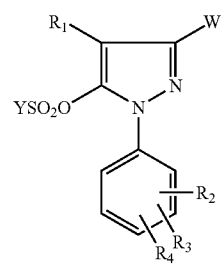

(IIIBb)

11. A compound as defined by formula (III):

(III)

in which:
  W represents a group —COOR or a radical —CN;
  Y represents a ($C_1$-$C_4$)alkyl group, a ($C_1$-$C_4$)perfluoroalkyl group or a phenyl group that is unsubstituted or substituted with a methyl, chloro or nitro group;
  $R_1$ represents a hydrogen or halogen atom or a ($C_1$-$C_4$) alkyl group;
  $R_2$, $R_3$ and $R_4$ each represent, independently of one another, a hydrogen or halogen atom or a ($C_1$-$C_4$)alkyl, ($C_1$-$C_4$)alkoxy or trifluoromethyl group;
  R represents a ($C_1$-$C_4$)alkyl or benzyl group.

12. The compound as recited in claim 11 defined by the formula (IIIA):

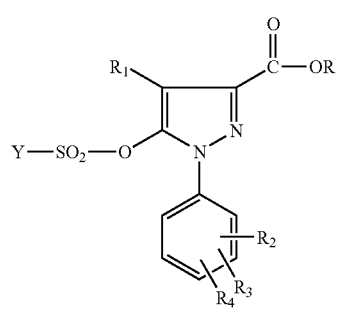

in which:
  Y, R, $R_1$, $R_2$, $R_3$ and $R_4$ are as defined in claim 11.

13. The compound as recited in claim 11 defined by the formula (IIIB):

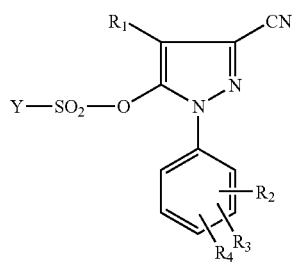

in which:
  Y, $R_1$, $R_2$, $R_3$ and $R_4$ are as defined in claim 11.

14. The compound as recited in claim 12, of formula (IIIAa):

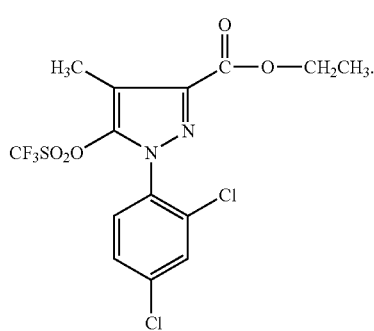

15. The compound as recited in claim 12, of formula (IIIAb):

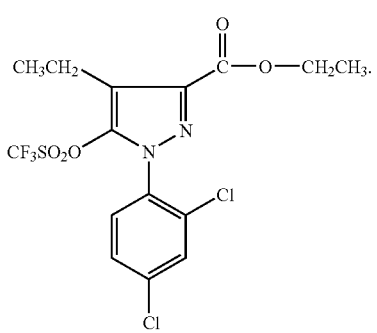

16. The compound as defined in claim 13, of formula (IIIBa):

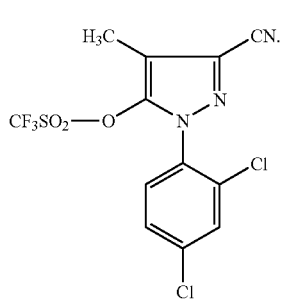

17. The compound as defined in claim 13, of formula (IIIBb):

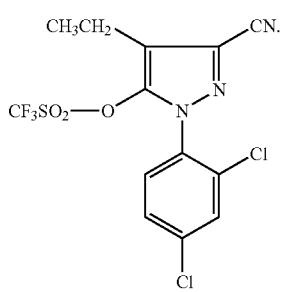

* * * * *